United States Patent
Hofman et al.

(10) Patent No.: US 9,682,119 B2
(45) Date of Patent: Jun. 20, 2017

(54) PEA-BASED PROTEIN MIXTURE AND USE THEREOF IN A LIQUID NUTRITIONAL COMPOSITION SUITABLE FOR ENTERAL FEEDING

(71) Applicant: N.V. Nutricia, Zoetermeer (NL)

(72) Inventors: Zandrie Hofman, Utrecht (NL); Rogier Daniël Van Anholt, Deventer (NL); Wynette Hermina Agnes Kiers, Zetten (NL); Thomas Ludwig, Utrecht (NL); Claudia Catharina Maria Van Den Braak, Utrecht (NL); Marianne Klebach, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 14/720,549

(22) Filed: May 22, 2015

(65) Prior Publication Data
US 2015/0250851 A1    Sep. 10, 2015

Related U.S. Application Data

(62) Division of application No. 13/266,736, filed as application No. PCT/NL2010/050236 on Apr. 27, 2010, now Pat. No. 9,066,537.

(30) Foreign Application Priority Data

Apr. 27, 2009  (WO) ................ PCT/NL2009/050227

(51) Int. Cl.
| | |
|---|---|
| A23L 1/305 | (2006.01) |
| A23L 1/29 | (2006.01) |
| A61K 38/16 | (2006.01) |
| A61K 36/48 | (2006.01) |
| A61K 38/01 | (2006.01) |
| A23L 33/00 | (2016.01) |
| A23L 33/185 | (2016.01) |
| A23L 33/19 | (2016.01) |

(52) U.S. Cl.
CPC ............ *A61K 38/16* (2013.01); *A23L 33/185* (2016.08); *A23L 33/19* (2016.08); *A23L 33/30* (2016.08); *A23L 33/40* (2016.08); *A61K 36/48* (2013.01); *A61K 38/018* (2013.01); *A61K 38/168* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,021,245 A | 6/1991 | Borschel et al. | |
| 5,486,461 A | 1/1996 | Nielsen | |
| 5,547,927 A | 8/1996 | Cope et al. | |
| 5,635,199 A | 6/1997 | Trimbo et al. | |
| 6,355,297 B1 | 3/2002 | Sawatzki et al. | |
| 6,468,579 B1 | 10/2002 | Roussel et al. | |
| 6,475,539 B1 | 11/2002 | DeWille et al. | |
| 6,489,310 B1 | 12/2002 | Brassart et al. | |
| 6,565,900 B2 | 5/2003 | Roussel et al. | |
| 6,846,501 B2 | 1/2005 | Prosise et al. | |
| 8,097,262 B2 | 1/2012 | Kuribayashi et al. | |
| 8,208,789 B2 | 6/2012 | Brodersen et al. | |
| 8,618,047 B2 | 12/2013 | Hofman et al. | |
| 2001/0018066 A1 | 8/2001 | Hahn | |
| 2003/0003194 A1 | 1/2003 | Roussel et al. | |
| 2003/0104033 A1 | 6/2003 | Lai et al. | |
| 2005/0152887 A1 | 7/2005 | Ernest | |
| 2006/0188643 A1 | 8/2006 | Solorio et al. | |
| 2008/0031860 A1 | 2/2008 | Hageman | |
| 2008/0206430 A1 | 8/2008 | Avila | |
| 2008/0226810 A1 | 9/2008 | Passe et al. | |
| 2010/0040739 A1 | 2/2010 | Kuribayashi et al. | |

(Continued)

FOREIGN PATENT DOCUMENTS

| | | |
|---|---|---|
| EP | 0 238 948 A2 | 9/1987 |
| EP | 0 553 389 B1 | 8/1993 |

(Continued)

OTHER PUBLICATIONS

Zhao et al., "Intestinal Transit and Absorption of Soy Protein in Dogs Depend on Load and Degree of Protein Hydrolysis," J. Nutr. 127:2350-2356 (1997).*
Sarosiek et al. "Safety of treatment for gastroparesis," Exp. Opin. Drug Safety 15:937-945 (2016).*
Abrahamsson, "Gastrointestinal motility disorders in patients with diabetes mellitus", Jounral of Internal Medicine, 1995, vol. 237, pp. 403-409.
Beaufrere, et al. "The 'Fast' and 'Slow' Protein Concept", Nestle Nutrition Workshop Series Clinical & Performance Program, 2000, vol. 3, pp. 121-133.
Calbet, et al. "Gastric emptying, gastric secretion and enterogastrone response after administration of milk proteins or their peptide hydrolysates in humans", Eur. J. Nutr., 2004, vol. 43, pp. 127-139.

(Continued)

*Primary Examiner* — Julie Ha
*Assistant Examiner* — Kristina M Hellman
(74) *Attorney, Agent, or Firm* — Gilberto M. Villacorta; Sunit Talapatra; Foley & Lardner LLP

(57) ABSTRACT

This invention relates to a pea-based protein mixture and use thereof in a liquid nutritional composition, in particular suitable for tube feeding, and further relates to the liquid nutritional composition for providing long-term complete enteral nutrition to patients in need thereof. More specifically, the pea-based protein mixture and the liquid nutritional composition comprising the pea-based protein mixture comprises more than 25 weight % and up to 80 weight % of vegetable protein comprising a source of intact pea protein and a source of intact soy protein. The invention relates further to a method for long-term enteral nutrition of patients in need thereof comprising administering an effective amount of the liquid nutritional composition comprising the pea-based protein mixture, in particular comprising a defined amount of intact pea protein and a second vegetable intact protein, other than pea protein.

18 Claims, 2 Drawing Sheets

(56) References Cited

U.S. PATENT DOCUMENTS

Figure 1:
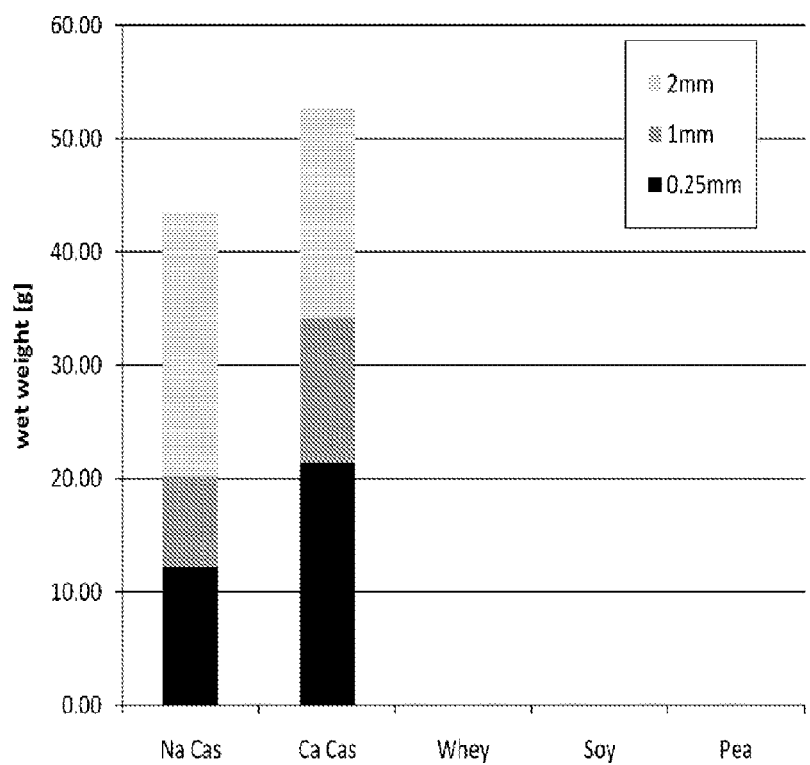

| | | |
|---|---|---|
| 2010/0086668 A1 | 4/2010 | Abrahamse et al. |
| 2010/0088252 A1 | 4/2010 | Le-Henand et al. |
| 2012/0283180 A1 | 11/2012 | Hofman et al. |
| 2012/0309831 A1 | 12/2012 | Van Anholt et al. |

FOREIGN PATENT DOCUMENTS

| | | |
|---|---|---|
| EP | 0 626 175 A2 | 11/1994 |
| EP | 0 626 175 B1 | 11/1994 |
| EP | 0 626 176 A2 | 11/1994 |
| EP | 1 059 040 B1 | 9/2006 |
| EP | 1 972 345 A1 | 9/2008 |
| EP | 1 972 346 A1 | 9/2008 |
| EP | 2 073 781 A2 | 7/2009 |
| EP | 2 424 384 B1 | 3/2012 |
| GB | 1 507 380 | 4/1978 |
| WO | WO-93/19624 A1 | 10/1993 |
| WO | WO-02/098242 A1 | 12/2002 |
| WO | WO-2004/047549 A1 | 6/2004 |
| WO | WO-2006/052134 A2 | 5/2006 |
| WO | WO-2007/004883 A2 | 1/2007 |
| WO | WO-2007/063142 A1 | 6/2007 |
| WO | WO-2008/032432 | 3/2008 |
| WO | WO-2008/046857 A1 | 4/2008 |
| WO | WO-2008/046871 A2 | 4/2008 |
| WO | WO-2009/072884 A1 | 6/2009 |
| WO | WO-2010/126353 A1 | 11/2010 |
| WO | WO-2010/126362 A1 | 11/2010 |
| WO | WO-2010/131952 A1 | 11/2010 |
| WO | WO-2011/093693 A1 | 8/2011 |

OTHER PUBLICATIONS

Caugant, et al. "In Vivo and In Vitro Gastric Emptying of Milk Replacers Containing Soybean Proteins", Journal of Dairy Science, 1994, vol. 77, No. 2, pp. 533-540.

Chavan, et al. "Functional properties of protein isolates from beach pea (*Lathyrus maritimus* L.)", Food Chemistry, 2001, vol. 74, pp. 177-187.

Decuypere, et al. "Influence of the Partial Replacement of Milk Protein by Soybean Protein Isolates with Different Physical Properties on the Performance and Nitrogen Digestibility of Early-Weaned Pigs", Journal of Animal Science, 1981, vol. 53, pp. 1011-1018.

Fachinformation Domperidon, 2002.

Fried, et al. "Decrease in gastric emptying time and episodes of regurgitation in children with spastic quadriplegia fed a whey-based formula", The Journal of Pediatrics, Apr. 1992, vol. 120, No. 4, pp. 569-572.

Gorrill, et al. "Body Weight Changes, Pancreas Size and Enzyme Activity, and Proteolytic Enzym Activity and Protein Digestion in Intestinal Contents from Calves Fed Soybean and Milk Protein Diets", The Journal of Nutrition, 1967, vol. 92, pp. 215-223.

Heyland, et al. "Canadian Clinical Practice Guidelines for Nutrition Support in Mechanically Ventilated, Critically Ill Adult Patients", Journal of Parenteral and Enteral Nutrition, Sep.-Oct. 2003, vol. 27, No. 5, pp. 355-373.

Hoffman, et al. "Protein—Which is Best?", Journal of Sports Science and Medicine, 2004, vol. 3, pp. 118-130.

International Search Report for PCT/NL2009/050227, dated Jan. 25, 2010.

International Search Report for PCT/NL2010/050236, dated Jul. 27, 2010.

International Search Report for PCT/NL2010/050241, dated Jun. 29, 2010.

International Search Report in PCT/NL2011/050060 dated Mar. 16, 2011.

Kiers, et al. "In vitro digestibility of Bacillus fermented soya bean", International Journal of Food Microbiology, 2000, vol. 60, pp. 163-169.

Koyoro, et al. "Functional Properties of Pea Globulin Fractions", Cereal Chem., 1987, vol. 64, No. 2, pp. 97-101.

Kreymann, et al. "ESPEN Guidelines on Enteral Nutrition: Intensive care", Clinical Nutrition, 2006, vol. 25, pp. 210-223.

Kwok, et al. "Review: effect of thermal processing on soymilk", Int. J. Food Sci. Tech., 1995, vol. 30, pp. 263-295.

Mahe, et al. "Gastrojejunal kinetics and the digestion of [15N]beta-lactoglobulin and casein in humans: the influence of the nature and quantity of the protein", The American Journal of Clinical Nutrition, 1996, vol. 63, pp. 546-552.

Meneses et al., "Evaluación biológica de la calidad de un mezcla de proteínas para use en nutrición enteral", Nut. Hosp., vol. 23, No. 3, Madrid, 2008, pp. 206-211. (Abstract).

Rombeau, et al. "Enteral and Tube Feeding", Clinical Nutrition, 2nd Edition, Chapter 8, pp. 160-167.

Schaffner, et al. "Functional Properties of Freeze-Dried Powders of Unfermented and Fermented Aqueous Extracts of Legume Seeds", Journal of Food Science, 1986, vol. 51, No. 3, pp. 629-633.

Souci, et al. "Food Composition and Nutrition Tables", Wissenschaftliche Verlagsgesellschaft mbH, 7, Auflage, 2008.

Westphal, et al. "Postprandial lipid and carbohydrate responses after the ingestion of a casein-enriched mixed meal", The American Journal of Clinical Nutrition, 2004, vol. 80, pp. 284-290.

WHO Technical Report Series 935, "Protein and Amino Acid Requirements in Human Nutrition: Report of a Joint FAO/WHO/UNU Expert Consultation," 2007, p. 241-247, p. 245, and Table 49.

WHO Technical Report Series No. 935, "Protein and Amino Acid Requirements in Human Nutrition", 2002.

Yvon, et al. "In Vitro Simulation of Gastric Digestion of Milk Proteins: Comparison between in Vitro and in Vivo Data", J. Agric. Food Chem, 1992, vol. 40, pp. 239-244.

Zayas, J. "Functionality of Proteins in Food", Springer, 1997 (TOC only).

Zayas, J. "Solubility of Proteins" Chapter 1, 1997, pp. 7-75.

Zuchner, "Ultra-Sensitive Protein Detection Unit: Working with proteins: protein stability and storage a brief guide", accessed Sep. 28, 2014 at URL unileipzig.de/uspdu/docs/Protein%20guide_Storage_Working.pdf.

* cited by examiner

PEA-BASED PROTEIN MIXTURE AND USE THEREOF IN A LIQUID NUTRITIONAL COMPOSITION SUITABLE FOR ENTERAL FEEDING

CROSS-REFERENCE TO RELATED APPLICATIONS

This application is a divisional application of U.S. application Ser. No. 13/266,736, filed Jan. 25, 2012, now allowed, which is the National Phase of International Patent Application No. PCT/NL2010/050236, filed Apr. 27, 2010 which claims priority to International Patent Application No. PCT/NL2009/050227, filed Apr. 27, 2009. The contents of these applications are herein incorporated by reference in their entirety.

BACKGROUND OF THE INVENTION

Field of the Invention

This invention relates to a pea-based protein mixture and use thereof in a liquid nutritional composition, in particular suitable for tube feeding, and further relates to said liquid nutritional composition for providing long-term complete enteral nutrition to patients in need thereof. More specifically, the pea-based protein mixture and the liquid nutritional composition comprising said pea-based protein mixture comprises a certain amount of an intact pea protein and a second intact vegetable protein, other than a pea protein. The invention relates further to a method for long-term enteral nutrition of patients in need thereof comprising administering an effective amount of said liquid nutritional composition comprising said pea-based protein mixture, in particular comprising a certain amount of an intact pea protein and a second intact vegetable protein, other than a pea protein.

Clinical Problem

Due to a variety of reasons, such as diseases, medical conditions, malnutrition, medical disabilities, post-surgery, etc. patients may not be able to obtain the necessary nutrition by ingesting food through the mouth, e.g. orally, by eating or drinking. Therefore, it has been known to provide medical enteral nutrition by oral nutritional supplements or tube feeding. Tube feeding is given to provide nutrition to patients which cannot obtain nutrition by swallowing, using a device such as a nasogastric feeding tube or a naso jejunal feeding tube, or by using a percutaneous endoscopic gastrostomy (PEG) or PEG—jejuno-feeding system. In the context of this application, the state of being fed by nutritional supplements and/or a by a feeding tube is called enteral feeding, comprising all of the abovementioned tube feeding systems, and the nutrition used in the feeding by nutritional supplements and/or a by a feeding tube is called enteral nutrition. Use of such enteral nutrition may be temporary for the treatment of acute conditions, or lifelong in the case of chronic disabilities. In the latter case, it is primordial that the enteral nutrition is designed for long-term administration containing all necessary components. In particular, the enteral nutrition contains a protein fraction which at least meets and preferably exceeds the WHO amino acid profile recommendations for complete nutrition. With advances in medicine resulting in increased life expectancy and better disease treatment, a large number of patients would benefit from such enteral nutrition designed to provide long-term enteral nutrition. Furthermore, said enteral nutrition should be easily digestible and not lead to upper gastrointestinal conditions or complications such as, e.g. intestinal discomfort, reflux, aspiration pneumonia, high gastric residual volume (GRV), vomiting, nausea, bloating, and delayed gastric emptying.

Technical Problem

It is the aim of the invention to provide a pea-based protein mixture which is suitable to be used in an enteral nutritional composition and which mimics a normal healthy protein diet containing a mix of different vegetable and animal proteins. In that respect, the pea-based protein mixture should contain at least 25 weight % of at least two different intact vegetable proteins, one of them being an intact pea protein, such that it offers a reduced dairy dependency and is more in agreement with the protein profile of a standard Western diet. Furthermore, the pea-based protein mixture should contain at most 75 weight % of dairy (i.e. animal milk-derived) protein. Furthermore, the pea-based protein mixture should meet the most recent (2007) WHO amino acid profile recommendations for complete nutrition (see: WHO technical report series no. 935—Protein and amino acid requirements in human nutrition: report of a joint FAO/WHO/UNU expert consultation, 2007, in particular Table 49 on page 245). Also, the pea-based protein mixture comprised in the enteral nutritional composition should be well-tolerated. Furthermore, the enteral nutritional composition comprising said pea-based protein mixture according to the invention should be easy to administer by tube, i.e. it should have a low viscosity and a low density, it should be pH neutral, have a good shelf stability, not segregate, agglomerate or precipitate. It should be suitable for heat treatments (such as sterilization and pasteurization) without a substantial change in structure, palatability (especially for oral nutritional supplements), viscosity, etc. The pea-based protein mixture should be easily mixable with other components, such as a fat fraction, a carbohydrate fraction, a digestible fibre fraction, and other components to provide a complete nutritional composition.

Surprisingly, the inventors have found that such pea-based protein mixture could be prepared from a source of intact pea protein and at least one other source of an intact vegetable protein other than said pea protein.

Background Prior Art

Meneses et al., Nutr. Hosp. Vol. 23 No. 3 Madrid May-June 2008 describe an experimental pea-based protein mixture comprising 50 weight % potassium caseinate, 25 weight % milk serum proteins and 25 weight % pea protein, to be used in enteral nutrition products. Said protein composition seems equivalent to the Vegenat SA product T-Diet Plus Estandar, comprising 2 g of caseinate, 1 g of whey and 1 g of pea protein per 100 ml of product.

EP 1 972 346 A1 (Katry Inversiones) discloses a pea-based protein mixture suitable for an enteral nutritional composition with a specific amino acid profile, to be used in enteral nutrition products, in particular a pea-based protein mixture comprising 50 weight % caseinate, 25 weight % milk serum proteins and 25 weight % pea protein. Katry does not teach to use more than 25 weight % of vegetal proteins, in particular pea proteins, nor does it teaches the combination of intact pea and other intact vegetable protein, nor the beneficial non-coagulating properties of the pea protein, the other intact vegetable protein or a combination thereof.

EP 1 059 040 A1 (Bongrain SA) discloses two liquid high protein mixtures from which solid and semi-solid nutritional products are formed by extrusion, the products comprising the proteins whey (12 weight %), casein (3.7 weight %), egg white (10 weight %), pea (4.1 weight %) and wheat (4.3 weight %); and whey (24 weight %), casein (3.2 weight %), egg white (1 weight %), pea (2.6 weight %), wheat (2.9 weight %) and soy (2.7 weight %), the rest being predominantly water.

U.S. Pat. No. 5,547,927 (Abbott) teaches an enteral nutritional product for patients undergoing radiation therapy and/or chemotherapy comprising hydrolysed soy (60 weight %), pea protein isolate (10 weight %) and whey protein concentrate (30 weight %). It also discloses not to use too much pea protein to avoid a too high viscosity of the resulting product.

US 2008/0031860 (NV Nutricia) teaches compositions for stimulating appetite comprising pea hydrolysate (40 weight %), soy protein (12 weight %) and potato protein (40 weight %), or a mixture of rice and pea protein hydrolysate. Said mixtures—disclosed in U.S. Pat. No. 5,547,927 and US 2008/0031860—do not contain intact pea protein.

US 2003/0104033 teaches enteral formulations comprising 40-95 weight % of caseinate and 5-60 weight % of a stabilizing protein, selected from the group of whey and a one or more vegetable proteins, selected from the group of soy, corn, potato, rice and pea, the most preferred vegetable protein being soy protein. The document is concerned with the reduction of creaming in enteral formulae, and no examples with pea protein are given.

None of these prior art protein mixtures comprise more than 25 weight % of vegetable proteins comprising at least a source of intact pea protein and a source of another intact vegetable protein.

SUMMARY OF THE INVENTION

In one embodiment, the present invention relates to a pea-based protein mixture, in particular for use in a nutritional composition suitable for tube feeding, comprising more than 25 weight % and up to 80 weight % of intact vegetable protein the protein mixture comprising at least a source of intact pea protein and a source of a second intact vegetable protein.

In another embodiment, the present invention relates to a liquid nutritional composition comprising the pea-based protein mixture according to the invention. Said liquid nutritional composition is particularly suitable for enteral feeding, in particular for long-term feeding.

Alternatively, the present invention relates to a liquid nutritional composition comprising more than 25 weight % and up to 80 weight % of intact vegetable protein which comprises at least a source of intact pea protein and a source of a second intact vegetable protein. Said liquid nutritional composition is particularly suitable for enteral feeding, in particular for long-term feeding.

Alternatively, the protein mixture according to the invention can suitable be used in the manufacture of a nutritional composition for the reduction of upper gastrointestinal conditions or complications selected from the group of intestinal discomfort, reflux, aspiration pneumonia, high gastric residual volume (GRV), vomiting, nausea, bloating, and delayed gastric emptying.

The invention will now be further elucidated by describing a number of embodiments of the present invention.

DETAILED DESCRIPTION OF THE INVENTION

Protein Mixture

Surprisingly, it was found that intact pea is substantially a non-coagulating protein in the stomach of a human person, which means that intact pea protein do not coagulate in the stomach of a human person under normal digestive conditions. Coagulation of proteins in the stomach is hypothesized to delay gastric emptying, This will result in upper gastrointestinal complications such as, e.g. intestinal discomfort, aspiration pneumonia, high gastric residual volume (GRV), vomiting, nausea, bloating, and delayed gastric emptying, especially in vulnerable persons, such as hospitalized patients. Hence, the finding that intact pea protein is a non-coagulating protein may provide a source of easily-digestible vegetable proteins.

Hence, according to one embodiment, the protein mixture according to the invention may be used in the manufacture of a nutritional composition for the reduction of upper gastrointestinal conditions or complications selected from the group of reflux, aspiration pneumonia, high gastric residual volume (GRV), vomiting, nausea, bloating, and delayed gastric emptying.

According to the invention, the protein mixture comprises more than 25 weight % and up to 80 weight % of intact vegetable protein comprising a source of intact pea protein and a source of a second intact vegetable protein.

In the context of this application, when referring to a "protein mixture", a "protein fraction", or a "protein composition" according to the invention, is meant a collection of proteins, proteinaceous matter, peptides and amino acids, free or in any bound form. Hence, the protein fraction of a nutritional composition is the sum of all proteins, proteinaceous matter, peptides and amino acids, free or in any bound form present in the nutritional composition. Furthermore, the wording "protein mixture" refers to a collection of proteins, proteinaceous matter, peptides and amino acids as such, in any form, as well as to a collection of proteins, proteinaceous matter, peptides and amino acids simultaneously present in another matrix, such as an aqueous matrix, such as a nutritional composition. In the latter case, the protein mixture may be referred to as a protein fraction of that matrix.

In the context of this application, the pea-based protein mixture consists essentially of intact vegetable and dairy proteinaceous matter, in particular proteins.

In the context of this application, the wording "vegetable" relates to protein from plant origin, such as, for instance originating from vegetables such as carrot, pea, chickpea, green pea, cowpea, field pea, kidney bean, lupine, rice, soy, canola, hemp, zein, maize, corn, barley, flax, linseed, and wheat. Equivalent wording may be used, such as "vegetal", "leguminous" or "plant-derived".

In the context of this application, the wording "dairy" protein relates to milk-derived protein, i.e. to protein derived from animal milk, such as derived from species such as camel, cow, goat, horse, human, reindeer, sheet, water buffalo and yak.

In one embodiment, the pea-based protein mixture according to the invention comprises 30 to 50 weight %, more in particular 35 to 45 weight % of intact vegetable protein relative to the total protein in the protein mixture.

The pea-based protein mixture according to the invention may have any physical form, such as a powder or liquid form, and it may be a solution, suspension, dispersion or the like. Preferably, the pea-based protein mixture according to the invention is in liquid form. Preferably, the pea-based protein mixture is an aqueous protein mixture.

Pea Protein

As stated above, surprisingly, it was found that intact pea protein is a non-coagulating protein in the stomach of a human person.

In the past, pea protein alone is generally classed as quite a poor vegetable source of protein, having a Biological Value (BV) of about 49% when compared to e.g. whole egg (100%), cow's milk (91%), casein (77%), soy (74%) and wheat (54%) (see e.g. Renner, E. (1983) Milk and dairy products in human nutrition. Volkswirtschaftlicher Verlag, Munich, Germany) and having an amino acid score (AAS) which is below the one for whole egg (1), cow's milk (1), casein (1) and soy (0.91). The BV of a protein is the amount of nitrogen used for tissue formation divided by the amount absorbed from the food and is expressed as a percentage.

The AAS is the ratio between the amount of the first limiting amino acid in the protein under study (mg/g) and the amount of that amino acid in a reference protein (mg/g), optionally multiplied by the true digestibility (Protein Digestibility Corrected-AAS, PDCAA). According to the WHO (2007) recommendations on protein quality as the reference, pea has an amino acid score of below 1.0 due to the relatively low methionine content. In all powders, pea protein tastes quite bad (even in intact form) and it doesn't mix too well, leaving a kind of grainy texture to the protein. However, the inventors have found that intact pea protein could be combined with one or more second intact vegetal proteins such as soy, in a concentration over and above 25 weight % and a dairy protein such as whey and/or casein, such that a good overall mix of amino acids could be obtained and an almost time-released composition. The whey proteins enter the blood stream very fast, while the pea proteins are absorbed much slower. Pea protein is relatively cheap (on the average, pea protein may cost about half the price of caseinates) and is added to the mixture to increase the protein content while keeping costs quite low. Pea protein is generally tolerated well by most people, it is lactose-free and is not a common allergen. Pea protein is quite high in cysteine content and can therefore compensate the inadequate amount of cysteine in casein proteins. Furthermore, pea protein is quite high in arginine compared to casein, soy or whey protein which is required for muscle metabolism and which facilitates the intake of body mass while reducing body fat; and it is quite high in lysine, when compared to the vegetable proteins, which is needed to build protein muscle and assist in the maintenance of lean body mass.

Several pea sources are readily available to the skilled person, for example, from Roquette (Lestrem, France) which markets a pea isolate obtained from the yellow pea (*Pisum sativum*), and from Cosucra Groupe Warcoing (Warcoing, Belgium).

Other pea protein sources may originate from green pea, cowpea, chickpea, and field pea.

According to the invention, the pea protein is substantially in intact form or non-hydrolysed.

In the context of this application, a "non-hydrolysed" protein is equivalent to an "intact" protein, meaning that the protein has not been subjected to an hydrolysis process. However, minor amounts of hydrolysed proteins may be present in the source of non-hydrolysed proteins, or may be added to the formulation, such as additional amino acids, such as, for example leucine, isoleucine, glutamine, arginine, or dipeptides and the like. In one embodiment of the present invention, the composition may comprise a free amino acid, or a mixture of free amino acids, up to 5 gram/100 ml, more preferably less than 2 gram/100 ml, more preferably less than 1 gram/100 ml, most preferably less than 0.5 gram/100 ml According to another embodiment, intact protein may only posses a degree of hydrolysis (DH) of 10% of lower, preferably 9, 8, 7, 6, 5, 4, 3, 2, 1% or lower.

In this context, "minor" should be understood as an amount of about 10 weight % or less. The term "about" should be interpreted as a deviation of plus or minus 10% of the given value.

According to another embodiment, the pea-based protein mixture according to the invention comprises 5 to 60 weight %, in particular 10 to 30 weight %, more in particular 15 to 25 weight % of intact pea protein, relative to the total protein in the protein mixture.

Second Vegetable Protein

The pea-based protein mixture according to the invention should further comprise a second intact vegetable protein, other than pea protein. Preferably, the second intact vegetable protein is selected from a group of soy, rice, and wheat protein. More preferably, the second intact vegetable protein is soy protein. According to the invention, the second intact vegetable protein is substantially in intact form, as defined above According to one embodiment of the invention, the second intact vegetable protein is substantially a non-coagulating protein in the stomach of a human person Soy Protein Surprisingly, it was found that intact soy is substantially a non-coagulating protein in the stomach of a human person, which means that intact soy protein do not coagulate in the stomach of a human person under normal digestive conditions. Coagulation of proteins in the stomach is hypothesized to delay gastric emptying, This will result in upper gastrointestinal complications such as, e.g. intestinal discomfort, aspiration pneumonia, high gastric residual volume (GRV), vomiting, nausea, bloating, and delayed gastric emptying, especially in vulnerable persons, such as hospitalized patients. Hence, the finding that intact soy protein is a non-coagulating protein may provide a source of easily-digestible vegetable proteins.

Soy protein has been used since 1959 as an ingredient for its functional properties in a variety of foods such as salad dressings, soups, vegetarian foods and meat imitations. Its functional properties are emulsification and texturizing. Recently, the popularity of soy protein is increasing, mainly because of its health benefits. It has been proven that soy protein can help to prevent cardiovascular problems and many countries allow health claims for food, which are rich in soy protein. Furthermore, health claims have been made for improving heart health (cholesterol reduction), improving bone health (increased bone density), menopausal symptom relief (reduced hot flashes), performance nutrition (faster muscle recovery) and weight management (satisfying hunger). Soy protein is a vegetable protein that contains the essential amino acids in a relatively high proportion for human health. Soy protein is categorized as a high-quality, complete protein although the methinione level is slightly below the WHO 2007 recommendation for methionine content. Soy proteins can be divided into different categories according to their production method. Soy protein isolate (SPI) is the most refined form of soy protein and is mainly used in meat products to improve texture and eating quality. Soy protein isolate contains about 90 percent protein. Soy protein concentrate (SPC) is basically soybean without the water soluble carbohydrates. It contains about 70 percent of protein. Textured soy protein (TSP) is made from soy protein concentrate by giving it some texture. TSP is available as dry flakes or chunks. It will keep its structure when hydrated. Hydrated textured soy protein chunks have a texture similar to ground beef. It can be used as a meat replacement or can be added to meat. Textured soy protein contains about 70 percent protein.

Several soy sources are readily available to the skilled person, for example, from The Solae Company (St. Louis, Mo., USA).

Dairy Proteins

According to one embodiment, the pea-based protein mixture according to the invention further comprises a dairy protein. Preferably, the dairy protein is selected from the group of casein and whey protein.

Preferably, the pea-based protein mixture according to the invention comprises 20 to 75 weight %, in particular 50 to 70 weight %, more in particular 55 to 65 weight % of at least one or more dairy proteins, relative to the total protein in the protein mixture.

Preferably, the dairy protein is included in substantially intact (unhydrolyzed) form, in order to have a palatable product. Such high molecular weight proteins increase the viscosity of the heat-treated liquid product, compared to the hydrolyzed forms. The present inventors were able to make a product with good palatability and low viscosity, by applying the measures according the invention.

Furthermore, the dairy proteins compensate for the relatively low methionine content of the vegetable proteins in order to have an amino acid score above 1.0 for the total protein mixture.

Whey Proteins

One of the most superior classes of food protein is whey protein. It is known for its excellent amino acid profile, for its ability to increase the protein synthesis in a mammal (due to a higher leucine content), for its improved tolerance and increased gastric emptying, and for its interesting bioactive proteins with immune enhancing properties (lactoglobulins, immunoglobulins, lysozyme, glutamine, cysteine and lactoferrins). Nutritionally speaking, whey protein is known as a naturally complete protein because it contains all of the essential amino acids required in the daily diet. It is also one of the richest sources of branched chain amino acids (BCAAs, in particular leucine) which play an important role in muscle protein synthesis. Moreover, some of the individual components of whey protein have been shown to prevent viral and bacterial infection and modulate immunity in animals. Whey protein is the preferred choice of proteins to treat persons suffering from sarcopenia, but is also suitable for healthy persons, such as sportsmen and active elderly. Furthermore, whey is also a non-coagulating protein, as defined above.

As a source of whey protein to be used in the present invention, any commercially available whey protein source may be used, i.e. whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat, lactose and glycomacroprotein (GMP), a casein-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used alone or in combination as source of globular whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source is available as a powder, preferably the whey protein source is a WPC or WPI.

Casein/Caseinate

Casein is one of the two types of protein found in milk, the other being whey. Casein separates from milk when milk is curdled, a process commonly carried out in the manufacturing of cheese, and is commonly called caseinate, having lost its typical micellar structure. Casein tends to form a gel in the stomach, which slows the digestion. This makes casein an ideal protein source to release protein into the bloodstream over a period of time, e.g. during sleep. Casein has also a high glutamine content, a conditionally essential amino acid, necessary for repair of muscle tissue after strenuous exercise and important for gut and immune function. Casein has a relatively low cysteine content which can be compensated by adding other proteins like vegetable proteins. Cysteine is important for the endogenous synthesis of glutathione and therefore plays an important role to protect damage from free radicals. Like many other nutritional compounds, casein is typically bound to a metal ion since the molecule is more stable this way. Specifically, casein is most commonly bound to calcium ($Ca^{2+}$) and sodium ($Na^+$) since all of these ions are found naturally in milk, or even potassium ($K^+$) or magnesium ($Mg^{2+}$), and tend to stick to the casein during the extraction process. Nutritionally, these compounds are basically interchangeable, as all forms of casein are effective protein sources. Micellar casein refers to casein in the form of native micelles. It is a high quality milk protein and naturally occurring in milk in a concentration of about 2.6 g/100 ml (Dairy Science and Technology, Walstra et al., CRC Press, 2006). It is concentrated by a process that does not, or does not substantially denature the casein proteins and it is marketed as Micellar Casein Isolate (MCI). Fresh skim milk is subjected to a microfiltration process, in much the same process used to concentrate whey protein, to produce a pure, substantially undenatured milk protein with its native structure. The resulting material contains between 90% and 95%, preferably more than 95% by weight of micellar casein, the rest mainly being whey protein and other non-protein nitrogen and other constituents, such as lactose and inorganic salts, in particular calcium phosphate. Within the context of this invention, it is understood that micellar casein may also be provided by other milk protein sources, such as, for instance, sources with essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk.

Within the context of this invention, with the term "casein" both caseinate and micellar casein is indicated.

In one embodiment, the casein is Na-caseinate or Ca-caseinate. Preferably, the caseinate is Ca-caseinate.

According to one embodiment, the protein mixture further comprises a dairy protein selected from the group of Na-caseinate, Ca-caseinate, micellar casein and whey protein.

Preferred Mixture

According to a preferred embodiment, the pea-based protein mixture according to the invention comprises casein, whey protein, intact soy protein and intact pea protein, wherein the protein mixture comprising more than 25 weight % and up to 80 weight % of intact vegetable proteins. Preferably, all proteins are in substantially intact form. According to a preferred embodiment, the pea-based protein mixture according to the invention comprises 20 to 40 weight % of casein, 20 to 40 weight % of whey protein, 13 to 25 weight % of intact soy protein, and 13 to 25 weight % of intact pea protein, relative to the total protein in the protein mixture, wherein the sum of said proteins equals 100 weight %. More preferably, the protein mixture according to the invention comprises about 25 weight % of casein, about 35 weight % of whey protein, about 20 weight % of intact soy protein, and about 20 weight % of intact pea protein, relative to the total protein in the protein mixture, wherein the sum of said proteins equals 100 weight %. The aforementioned pea-based protein mixture has an excellent amino acid profile.

Amino Acid Profile

The pea-based protein mixture according to the invention at least meets and preferably exceeds the WHO amino acid profile recommendations for complete nutrition.

In one embodiment, the pea-based protein mixture according to the invention has the following amino acid profile in gram per 100 gram total protein in the protein mixture:

Cysteine: at least 1.1 g/100 g
Phenylalanine: at least 4.0 g/100 g
Tyrosine: at least 3.7 g/100 g.

In another embodiment, the pea-based protein mixture according to the invention has the essential amino acid profile range as given in Table 1 in gram per 100 gram total protein in the protein mixture. In the right column, the minimum amount according to WHO 2007 Guidelines is given.

TABLE 1

| Amino acid (essential and semi-essential) | Range according to invention (g/100 g) | Minimum amount (WHO, 2007)[a] (g/100 g) |
|---|---|---|
| Histidine | 2.0 to 2.6 | 1.5 |
| Isoleucine | 5.2 to 6.4 | 3.0 |
| Leucine | 9.0 to 11.0 | 5.9 |
| Lysine | 7.5 to 9.0 | 4.5 |
| Methionine | 1.7 to 2.3 | 1.6 |
| Cysteine | 1.1 to 1.7 | 0.6 |
| Threonine | 4.9 to 6.2 | 2.3 |
| Tryptophan | 1.2 to 1.6 | 0.6 |

TABLE 1-continued

| Amino acid (essential and semi-essential) | Range according to invention (g/100 g) | Minimum amount (WHO, 2007)[a] (g/100 g) |
|---|---|---|
| Valine | 5.5 to 6.9 | 3.9 |
| Phenylalanine | 4.2 to 5.2 | Phe + Tyr = 3.0 |
| Tyrosine | 3.7 to 4.7 | |

[a]based on mean nitrogen requirement of 105 mg nitrogen/kg per day (0.66 g protein/kg body weight per day).

In a further embodiment, the pea-based protein mixture according to the invention has the amino acid profile range as given in Table 2 in gram per 100 gram total protein in the protein mixture, or the specific amino acid profile as given in the right column of Table 2.

TABLE 2

| Amino acid (essential, semi-essential and non-essential) | Range according to invention (g/100 g) | Specific amino acid profile (g/100 g) |
|---|---|---|
| Histidine | 2.0 to 2.6 | 2.3 |
| Isoleucine | 5.2 to 6.4 | 5.8 |
| Leucine | 9.0 to 11.0 | 9.8 |
| Lysine | 7.5 to 9.0 | 8.3 |
| Methionine | 1.7 to 2.3 | 2.0 |
| Cysteine | 1.1 to 1.7 | 1.4 |
| Threonine | 4.9 to 6.2 | 5.6 |
| Tryptophan | 1.2 to 1.6 | 1.4 |
| Valine | 5.5 to 6.9 | 6.2 |
| Phenylalanine | 4.2 to 5.2 | 4.8 |
| Tyrosine | 3.7 to 4.7 | 4.1 |
| Alanine | 4.0 to 5.1 | 4.6 |
| Arginine | 4.5 to 5.7 | 5.2 |
| Aspartic Acid/Asparagine | 9.5 to 11.7 | 10.7 |
| Glutamic acid/Glutamine | 18.0 to 22.8 | 20.2 |
| Glycine | 2.6 to 3.2 | 2.9 |
| Proline | 5.8 to 7.3 | 6.5 |
| Serine | 5.3 to 6.5 | 5.9 |

Preparation of the Preferred Protein Mixture

The pea-based protein mixture according to the invention is prepared by mixing the pea protein and one or more individual proteins in powder form with water, for instance by dumping the individual powder proteins out of Totebin® containers into water, optionally comprising soluble carbohydrates, such as maltodextrins, and mixing the resulting solution. The temperature of the water, optionally comprising carbohydrates, is preferably between about 20 and about 60 degrees Celsius. For instance, when a maltodextrine syrup is used, the temperature is about 60 degrees Celsius, being the temperature of the syrup. The carbohydrates may also be added at a later stage.

In principle, the protein mixture has now been prepared, but further ingredients may be added, such as minerals, fibres, fat, etc.

Pasteurization of the protein mixture may be conducted without substantially raising its viscosity. For instance, pasteurization may be done for 30 seconds at 85° C., followed by a homogenization at 550 bar pressure, followed by cooling down the solution to 4 to 20° C.

The pH of the resulting solution may be adjusted, for instance to pH=8, and the resulting solution may be further sterilized in an autoclave. The time/temp profile is dependent on the type of packaging, the resulting product and the F0-value, for instance for a bottled product the time/temperature profile is 121.5 to 122.5° C. during 16 minutes.

Characterisation of the Protein Mixture

The protein mixture according to the invention and its quality is characterised by determining the Protein Digestibility Corrected Amino Acid Score (PDCAAS) using the essential amino acid content of the different individual protein sources, their digestibility and the WHO 2007 amino acid recommendations as reference (see Experimental, Table 4).

Nutritional Composition

Surprisingly, the pea-based protein mixture according to the invention makes it possible to produce a nutritional composition, in particular a liquid enteral nutritional composition with a long shelf life and with a low viscosity, more in particular a tube feed. Hence, the invention also pertains to a pea-based protein mixture according to the invention for use in the manufacture of a nutritional composition, in particular a liquid nutritional composition, in particular for use as a tube feed, most in particular for long-term tube feeding.

Most preferably, such liquid nutritional composition is sterilized or pasteurized.

In one particular embodiment, the invention relates to a liquid nutritional composition comprising
20 to 40 weight % of casein,
20 to 40 weight % of whey protein,
13 to 25 weight % of intact soy protein and
13 to 25 weight % of intact pea protein,
relative to the total protein in the protein mixture, wherein the sum of said proteins equals 100 weight %.

In another particular embodiment, the invention relates to a liquid nutritional composition comprising
about 25 weight % of casein,
about 35 weight % of whey protein,
about 20 weight % of intact soy protein, and
about 20 weight % of intact pea protein,
relative to the total protein in the protein mixture, wherein the sum of said proteins equals 100 weight %.

In the context of this application, the % of total energy is also abbreviated as En %; En % is thus short for energy percentage and represents the relative amount that a constituent contributes to the total caloric value of the composition.

In the context of this application, the term "at least" also includes the starting point of the open range. For example, an amount of "at least 95 weight %" means any amount equal to 95 weight % or above.

In the context of this application, the term "about" defines a range of plus or minus 10% of the cited value. For example, an amount of "about 20 weight %" means any amount within the range of 18 to 22 weight %.

Preferably, the liquid nutritional composition according to the invention comprises the pea-based protein mixture according to the invention, which pea-based protein mixture comprises at least 8 En %, preferably at least 10 En %, more preferably at least 15 En % of the total energy of the composition.

Preferably, the liquid nutritional composition according to the invention comprises at least 0.4 kcal/ml, preferably at least 0.7 kcal/ml, most preferably at least 0.9 kcal/ml.

The composition according to the invention is designed to either supplement a person's diet or to provide complete nutritional support. Hence, the composition according to the invention may further comprise at least fat and/or carbohydrate and/or a source of vitamins and minerals and/or a source of prebiotics. Preferably, the composition according the invention is a nutritionally complete composition.

Viscosity

In one embodiment of the present invention, the viscosity of the liquid enteral nutritional composition is lower than 500 mPa·s, measured at 20° C. (i.e. room temperature) at a shear rate of 100 s$^{-1}$, preferably between 10 and 200 mPa·s, more preferably between 10 and 100 mPa·s, most preferably below 50 mPa·s. The viscosity may suitably be determined using a rotational viscosity meter using a cone/plate geometry. This viscosity is ideal for orally administering the liquid enteral nutritional composition according to the invention because a person may easily consume a serving having a low viscosity such as that displayed by the present invention. This viscosity is also ideal for unit dosages that are tube fed.

In one embodiment of the present invention, the density of the composition ranges between 1.00 g/ml and 1.20 g/ml, especially between 1.05 g/ml and 1.15 g/ml.

Dosage Unit

The liquid enteral nutritional composition according to the invention preferably has the form of a complete food, i.e. it can meet all nutritional needs of the user. As such, the liquid enteral nutritional composition according to the invention preferably contains 1000 to 2500 kcal per daily dosage. Depending on the condition of the patient, a daily dose is about 25 to 35 kcal/kg bodyweight/day. Therefore, a typical daily dose for a 70 kg person contains about 2000 kcal. The complete food can be in the form of multiple dosage units, e.g. from 8 (250 ml/unit) to 2 units (1 l/unit) per day for an energy supply of 2000 kcal/day using a liquid enteral nutritional composition according to the invention of 1.0 kcal/ml. Preferably, the nutritional composition is adapted for tube feeding.

In the case the liquid enteral nutritional composition is an oral food supplement, it can for example to be used in addition to a non-medical food or normal diet. Preferably, as an oral supplement, the liquid enteral nutritional composition contains per daily dosage less than 1500 kcal, in particular as a supplement, the liquid enteral nutritional composition contains 500 to 1000 kcal per daily dose. The food supplement can be in the form of multiple dosage units, e.g. from 2 (250 ml/unit) to 10 units (50 ml/unit) per day for an energy supply of 500 kcal/day using a liquid enteral nutritional composition according to the invention of 1.0 kcal/ml.

Preferably, the nutritional composition is packaged, stored and provided in a container such as plastic bag or a pouch or the like. A variety of such containers is known, for example 500 ml, 1000 ml, and 1500 ml containers are known in the art. It should be noted that any suitable container can be used to package, store and provide the nutritional composition according to the invention.

In one embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

Effectivity

The present invention also concerns a method of providing nutrition to a person in need thereof, comprising the steps of administering to said person the nutritional composition according to the present invention. Said person may be an elderly person, a person that is in a disease state, a person that is recovering from a disease state, or a person that is malnourished.

The present invention is also related to providing long-term tub-fed nutrition to patients in need thereof. As used herein, the term "long-term" means greater than one month (30 days). It is obvious that nutrition, when suitable for long-term nutrition, is also suitable for any other shorter period of nutrition, such as medium-term nutrition (10 to 30 days) and short-term nutrition (between 1 and 10 days). However, tube nutrition is designed for maintenance patients. As used herein, "maintenance patient" refers to an patient, being any human of any age, in particular children, adults and elderly, who is unable to receive nutrition through a normal diet but who is normo-metabolic, i.e. not suffering from a metabolic disorder. As used herein, the term "normal diet" means to receive at least substantially all nutrition by eating, i.e. e.g. orally, by eating or drinking. Because the long term enteral nutritional composition according to the invention is provided for maintenance, it is not directed to treatment of any specific disorder, such as cancer, HIV, diabetes, e.a. Patients are typically stable, normo-metabolic, healthy patients except for the fact that they require enteral nutrition in order to meet the necessary nutritional requirements. Hence, these patients may suffer from a variety of disorders including swallowing disorders of a variety of etiologies, particularly surgical consequences of ear/nose/throat cancer, and patients suffering from a cerebral vascular accident.

The invention will now be further elucidated by several examples, without being limited thereby.

LIST OF FIGURES

FIG. 1: Absolute wet weight of coagulates after 100 minutes of gastric digestion.

Figure 2:
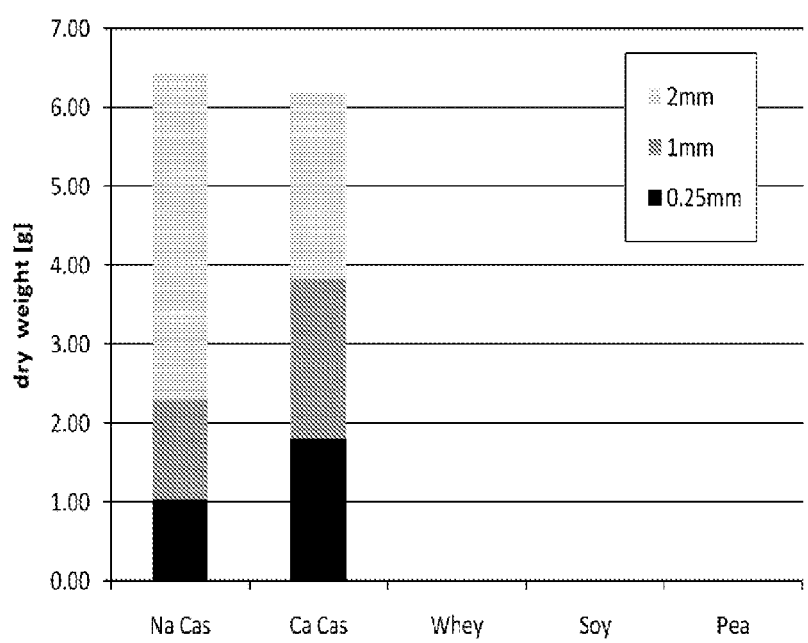

FIG. 2: Absolute dry weight of coagulates after 100 minutes of gastric digestion.

Figure 3:
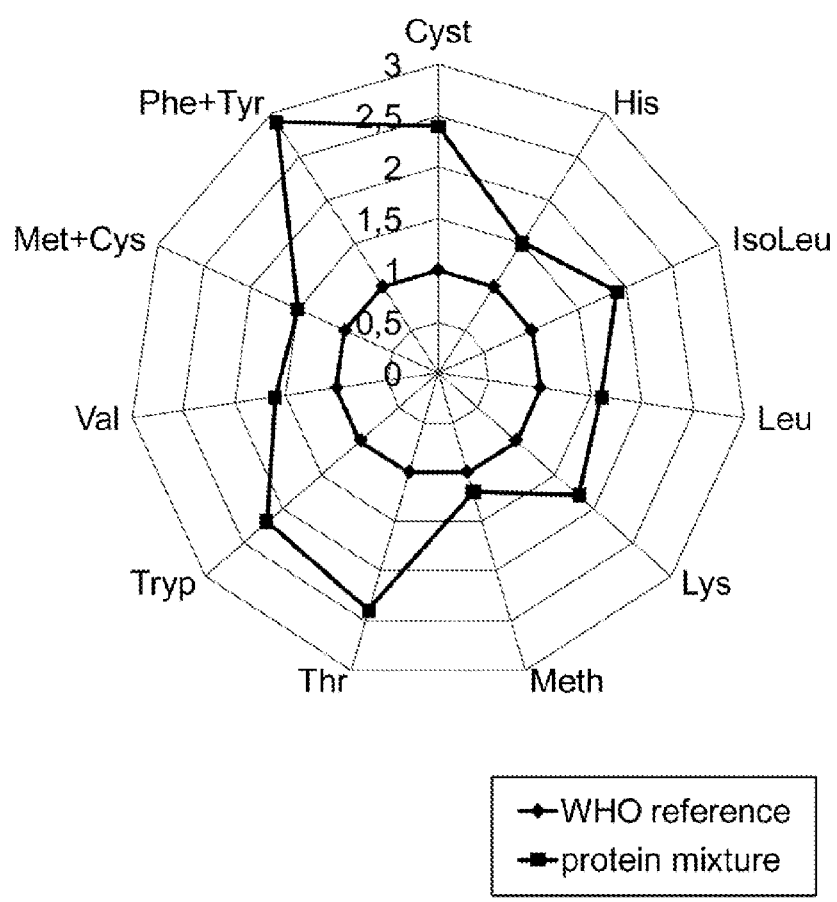

FIG. 3: Aminogram based on the PDCAAS data for Example B1. Outer line: Protein mixture of Example B1; Inner line: WHO 2007 reference.

EXAMPLES

Example A: Non-Coagulating Behavior of Pea Protein

Experimental Study Outline

The coagulation properties upon gastric digestion were investigated for homogenized and heat treated protein solutions consisting of 6% (w/v) of sodium caseinate, calcium caseinate, whey, intact pea, and intact soy.

Gastric Digestion

Stomach digestion was mimicked over 100 minutes in a computer controlled substrate pump setup (Multifermentor fed-batch; DASGIP AG, Juelich, Germany) at 37° C. upon continuous stirring.

For each experiment, 150 ml of protein solution were used as the starting volume. Per experiment, a total of 45 ml of artificial stomach juice (50 mM NaCl, 15 mM KCl, 1 mM $CaCl_2.H_2O$, 15 mM $NaHCO_3$, 0.014% (w/v) pepsin (porcine stomach, sigma p7012), 0.019% (w/v) lipase (*Rhizopus oryzae*, DF 15K Amano Pharmaceutical Co, Ltd Nagoya); pH 4.0) was added. The stomach juice was added in two steps with different flow rates. In the first two minutes, a flow rate of 225 ml/h was used. For the rest of the experiment the flow rate was 23 ml/h. In addition, in the first 60 minutes of the experiment a total of 30 ml of artificial saliva (0.1 M NaCl, 30 mM KCl, 2 mM $CaCl_2.2H_2O$, 15 mM $NaHCO_3$, 0.065% (w/v) α-amylase (Sigma A 6211); pH 6.3) was added continuously to the solution.

The pH was decreased over 100 minutes from a pH of 6.6 at start to a final pH of 2.0 (pH at start=6.6, pH at 8 minutes=5.0, at 15 minutes=4.0, at 42 minutes=3.0, at 100 minutes=2.0) by the addition of 1 M HCl upon continuous mixing. If necessary, acidification was automatically corrected by the addition of an alkaline solution (1 M $NaHCO_3$, 3 M NaOH).

Determination of Coagulate

After gastric digestion, the samples were poured over metal sieves to yield fractions with particle sizes of a) bigger than 2 mm, b) below 2 mm and above 1 mm, c) below 1 mm and above 0.25 mm and d) below the limit of 0.25 mm. Fractions a) to c) constitute what is here referred to as coagulate. The wet and dry weight of these three fractions was determined separately. In short, after determining the wet weight the dry weight was determined according to Monjonnier. Samples were gently heated to evaporate the water and subsequently placed in a vacuum oven. The residue constitutes the absolute dry weight of the sample.

All experiments were performed in triplicate.

Results

Results are given as mean±SEM. Sodium caseinate yielded 43.5±0.9 g of total wet coagulate (FIG. 1) and 6.4±0.6 g of total dry coagulate (FIG. 2). Calcium caseinate yielded 52.8±7.5 g of total wet coagulate (FIG. 1) and 6.2±0.7 g of total dry coagulate (FIG. 2). Whey, soy, and pea did not produce any measurable wet or dry coagulate (FIGS. 1 and 2).

Example B

The following protein compositions can suitably be used as an enteral composition according to the invention, respectively as adult tube feed, as paediatric tube feed and as an adult oral nutritional supplement (Table 3).

TABLE 3

| Component | Ex. B1 Adult tube feed | Ex. B2 Paediatric tube feed | Ex. B3 Adult Oral nutritional supplement |
|---|---|---|---|
| Energy value | | | |
| (kcal/100 ml) | 100 | 100 | 240 |
| Protein | | | |
| (g/100 ml) | 4 | 2.5 | 9.6 |
| (En %) | 16 | 10 | 16 |
| Pea protein | 0.8 g/100 ml | 0.50 g/100 ml | 1.92 g/100 ml |
| Whey protein | 1.4 g/100 ml | 0.87 g/100 ml | 3.36 g/100 ml |
| Casein | 1.0 g/100 ml | 0.63 g/100 ml | 2.40 g/100 ml |
| Soy protein | 0.8 g/100 ml | 0.50 g/100 ml | 1.92 g/100 ml |
| Carbohydrates | 12.3 g/100 ml (49 En %) | 12.5 g/100 ml (50 En %) | 29.7 g/100 ml (49 En %) |
| Fat | 3.9 g/100 ml (35 En %) | 4.4 g/100 ml (40 En %) | 9.3 g/100 ml (35 En %) |
| Fibre | 1.5 g/100 ml | none | none |
| Viscosity | 18 mPa · s | 12 mPa · s | 25 mPa · s |
| Density | 1.06 kg/l | — | — |

The composition is supplemented with appropriate amounts of minerals, trace elements and vitamins, carotenoids and choline to provide a complete nutritional composition Quality Determination The protein mixture used Example B1 (adult tube feed) and its quality was characterised by determining the Protein Digestibility Corrected Amino Acid Score (PDCAAS) using the essential amino acid content of the different individual protein sources, their digestibility and the WHO 2007 amino acid recommendations as reference. The PDCAAS of this protein mixture is the lowest PDCAAS value of the individual amino acids, which is 1.2 (Table 4).

TABLE 4

| | Casein | Soy | Whey | Pea | WHO 2007 reference AA pattern | PDCAAS |
|---|---|---|---|---|---|---|
| Cysteine | 0.40 | 1.20 | 2.60 | 1.00 | 0.6 | 2.4 |
| Histidine | 3.10 | 2.50 | 1.55 | 2.30 | 1.5 | 1.5 |
| Isoleucine | 5.80 | 5.10 | 7.20 | 4.10 | 3.0 | 1.9 |
| Leucine | 10.10 | 8.40 | 11.80 | 7.60 | 5.9 | 1.6 |
| Lysine | 8.40 | 5.60 | 10.70 | 6.70 | 4.5 | 1.8 |
| Methionine | 2.90 | 1.40 | 2.40 | 0.90 | 1.6 | 1.2 |
| Threonine | 4.60 | 3.90 | 8.60 | 3.50 | 2.3 | 2.4 |
| Tryptophan | 1.40 | 1.30 | 1.65 | 0.90 | 0.6 | 2.2 |
| Valine | 7.50 | 5.10 | 6.80 | 4.50 | 3.9 | 1.6 |
| Met + Cys | 3.30 | 2.60 | 5.00 | 1.90 | 2.2 | 1.5 |
| Phe + Tyr | 11.20 | 9.40 | 7.15 | 8.30 | 3.0 | 2.9 |
| Digestibility (%) | 98 | 98 | 98 | 98 | | |

Using these PDCAAS data, the concomitant aminogram is shown in FIG. 3.

It should be understood that various changes and modifications to the presently preferred embodiments described herein will be apparent to those skilled in the art. Such changes and modifications may be made without departing from the spirit and scope of the invention and without diminishing its advantages. It is therefore intended that such changes and modifications are covered by the appended claims.

The invention claimed is:

1. A method for the reduction of reflux, aspiration pneumonia, high gastric residual volume (GRV), vomiting, nausea, bloating, and/or delayed gastric emptying in a subject in need thereof, the method comprising administering to the subject a heat-sterilized or heat-pasteurized protein mixture comprising, based on total protein in the mixture, 25 to 80 weight % of intact vegetable proteins selected from at least two different vegetables, one of which is pea.

2. The method according to claim 1, wherein the protein mixture comprises 30 to 50 weight % of intact vegetable proteins, based on total protein weight in the mixture.

3. The method according to claim 1, wherein the protein mixture comprises 35 to 45 weight % of intact vegetable proteins, based on total protein weight in the mixture.

4. The method according to claim 1, wherein the protein mixture comprises 5 to 60 weight % of intact pea protein, based on total protein weight in the mixture.

5. The method according to claim 4, wherein the protein mixture comprises 10 to 30 weight % of intact pea protein, based on total protein weight in the mixture.

6. The method according to claim 5, wherein the protein mixture comprises 15 to 25 weight % of intact pea protein, based on total protein weight in the mixture.

7. The method according to claim 1, wherein the protein weight mixture comprises intact pea protein and intact soy protein.

8. The method according to claim 1, wherein the protein weight mixture further comprises 20 to 75 weight % dairy protein, based on total protein in the mixture.

9. The method according to claim 8, wherein the protein mixture comprises 50 to 70 weight % dairy protein, based on total protein weight in the mixture.

10. The method according to claim 9, wherein the protein mixture comprises 55 to 65 weight % dairy protein, based on total protein weight in the mixture.

11. The method according to claim 1, wherein the protein mixture comprises intact pea protein, intact soy protein, casein and whey protein.

12. The method according to claim 1, wherein the protein mixture comprises:
 (a) 20 to 40 weight % of casein,
 (b) 20 to 40 weight % of whey protein,
 (c) 13 to 25 weight % of intact soy protein, and
 (d) 13 to 25 weight % of intact pea protein,
 based on total protein weight in the protein mixture, wherein the sum of the proteins (a)-(d) equals 100 weight %.

13. The method according to claim 1, wherein the composition is a nutritional composition, and wherein the protein mixture comprises at least 8 en % of the total energy of the composition.

14. The method according to claim 13, wherein the composition is a nutritional composition, and wherein the protein mixture comprises at least 10 en % of the total energy of the composition.

15. The method according to claim 1, wherein the composition is a nutritional composition, having an energy content of at least 0.4 kcal/ml of composition.

16. The method according to claim 15, wherein the composition has an energy content of at least 0.7 kcal/ml of composition.

17. The method according to claim 1, wherein the administration is by tube feeding.

18. The method according to claim 1, wherein the subject is a human being.

* * * * *